United States Patent [19]

Hudrlik

[11] Patent Number: 5,243,981
[45] Date of Patent: Sep. 14, 1993

[54] MYOCARDIAL CONDUCTION VELOCITY RATE RESPONSIVE PACEMAKER

[75] Inventor: Terrence R. Hudrlik, Fridley, Minn.
[73] Assignee: Medtronic, Inc., Minneapolis, Minn.
[21] Appl. No.: 912,352
[22] Filed: Jul. 13, 1992
[51] Int. Cl.[5] ........................................... A61N 1/368
[52] U.S. Cl. ....................................... 607/11; 607/27
[58] Field of Search ............. 128/419 PG, 419 P, 734, 128/642

[56] References Cited

U.S. PATENT DOCUMENTS

| | | | |
|---|---|---|---|
| 4,228,803 | 10/1980 | Rickards | 128/419 PG |
| 4,543,954 | 10/1985 | Cook et al. | 128/419 PG |
| 4,688,573 | 8/1987 | Alt | 128/419 PG |
| 4,708,143 | 11/1987 | Schroeppel | 128/419 PG |
| 4,712,555 | 12/1987 | Thornander | 128/419 PG |
| 4,750,494 | 6/1988 | King | 128/419 PG |
| 4,759,367 | 7/1988 | Callaghan | 128/419 PG |
| 4,856,522 | 8/1989 | Hansen | 128/419 PG |
| 4,892,102 | 1/1990 | Astrinsky | 128/419 PG |
| 4,936,304 | 6/1990 | Kresh et al. | 128/419 PG |
| 5,052,388 | 10/1991 | Sivula et al. | 128/419 PG |
| 5,063,927 | 11/1991 | Webb et al. | 128/419 PG |
| 5,074,303 | 12/1991 | Hauck | 128/419 PG |
| 5,156,149 | 10/1992 | Hudrlik | 128/419 PG |

OTHER PUBLICATIONS

"Bioelectric Amplifiers" in Introduction To Biomedical Equipment Technology by Carr and Brown, John Wiley & Sons, 1981, pp. 41-44.

Primary Examiner—William E. Kamm
Assistant Examiner—George Manuel
Attorney, Agent, or Firm—Reed A. Duthler; Harold R. Patton

[57] ABSTRACT

A system for detecting changes in the myocardial conduction velocity and deriving control signals therefrom for controlling the delivery of electrical or other therapy to the heart or for monitoring or diagnostic purposes. The system comprises two spaced electrodes coupled to amplifiers which detect the relative arrival times of the depolarization wavefront at the electrodes, measurement circuitry for measuring the difference in arrival times to determine conduction velocity circuitry for deriving control signals for controlling operation of an implantable medical device as a function of measured conduction velocity. The particular embodiment disclosed is a cardiac pacer in which the measured conduction velocity is used to control pacing rate.

19 Claims, 2 Drawing Sheets

MYOCARDIAL CONDUCTION VELOCITY RATE RESPONSIVE PACEMAKER

CROSS REFERENCE TO RELATED APPLICATIONS

Attention is drawn to the commonly assigned copending U.S. Pat. application Ser. No. 07/566,636, now continuation application Ser. No. 07/827,858 for a "Field Density Clamp for Sensing Cardiac Depolarizations", filed Aug. 10, 1990 in the name of Terrence R. Hudrlik, U.S. Pat. application Ser. No. 07/626,061, for "Electronic Capture Detection for a Pacer", filed Dec. 12, 1990 and U.S. Pat. application Ser. No. 07/730,160, for a "Medical Stimulator With Operational Amplifier Output circuit", filed Jul. 15, 1991 in the name of Terrence R. Hudrlik, all three of which are incorporated herein in by reference in their entireties.

BACKGROUND OF THE INVENTION

This invention relates to implantable diagnostic and tissue stimulation devices such as implantable pacemakers, cardioverters and defibrillators, implantable monitoring devices and implantable drug dispensers, and more particularly to rate-responsive implantable pacemakers that vary their pacing rate as a function of the patient's metabolic demand for oxygenated blood.

Early pacemakers provided a fixed rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operations, delivering pacing stimuli to the atrium and/or ventricle at fixed rates or rates that vary between an upper rate limit and a lower rate limit.

More recently, single and dual chamber pacemakers have been developed that respond to physiologic sensors which, with greater or lesser degree of specificity, sense the body's need to deliver more or less oxygenated blood to the cardiovascular system. For example, rate responsive pacing systems have been developed and marketed which rely upon the central venous blood temperature, as measured in the right ventricle. Such pacemakers are disclosed in U.S. Pat. No. 4,688,573 issued to Alt and U.S. Pat. No. 4,543,954 issued to Cook et al.

It has been proposed in the prior art to measure the time interval between an atrial stimulation pulse, A, and the responsive atrial or ventricular depolarization, P or R, respectively, as an indication of the physiological demands placed on the heart. The time interval between a ventricular stimulation pulse, in, and the responsive ventricular depolarization, R, is also proposed to be measured and used as an indication of physiologic need. The atrial depolarization is sensed by detecting a P-wave wherein the ventricular depolarization is sensed by detecting an R-wave. U.S. Pat. No. 4,712,555 sets forth such a system which includes the further method of measuring the A-P or A-R to ascertain whether the intervals are increasing or decreasing. If over several heart cycles or beats, an increase or decrease in these measurements is detected, the pacing interval set by the pacemaker is adjusted in an appropriate direction in order to adjust the heart stimulation rate accordingly. In the '555 patent, atrial and ventricular bipolar sense/pace electrodes are distributed in the right atrium and ventricle of the heart, and the measurements are taken by way of conventional pacemaker sense amplifiers.

It has also been proposed in the prior art to measure the evoked potential following the application of a pacing stimulus and to employ its amplitude and/or configuration to regulate automatically the implantable cardiac pacemaker's output characteristics, such as rate. U.S. Pat. No. 4,759,367 describes such a cardiac pacing system which combines unipolar and bipolar electrode configurations to detect the evoked potential and apply the pacing stimulus respectively. It is suggested therein that a bipolar lead may be placed in the atrium or the ventricle or a pair of such bipolar leads may be placed in either chamber for dual chamber pacing.

In the '367 patent, it is proposed that the magnitude of the evoked response be integrated over time to obtain a repolarization gradient value. The rate control algorithm involves comparing the measured repolarization gradient magnitude of the current cardiac cycle with a stored repolarization gradient magnitude of at least one previous cardiac cycle. It is known that with conventional sense amplifiers of the type shown in the '367 patent having a high input impedance that one may detect and integrate the varying amplitude of the relatively wide QRST waveform relatively easily. However, it is difficult to use such sense amplifiers to consistently identify the same point in the QRST wavefront in order to develop a time interval representative of the myocardial conduction velocity.

In this regard, attention is also drawn to Rickards U.S. Pat. No. 4,228,803 which relies upon the detection of time intervals following the delivery of a pacing stimulus to develop a rate control signal to either increase or decrease the pacing rate. In the '803 patent, the system measures the stimulus to repolarization (i.e. T-wave) interval, otherwise known as the QT interval. Again, in these patents and in the products which have been developed and marketed implementing them, conventional high input impedance sense amplifiers have been employed to detect the evoked response.

In U.S. Pat. No. 4,750,494 issued to King, conventional sense amplifiers are used to detect arrival times of depolarization wavefronts at multiple electrode sets are in order to measure changes in depolarization wavefront propagation direction, as part of a system for detecting impending fibrillation. If the net direction of the depolarization wavefront changes by more than a predetermined amount, the device determines that fibrillation is likely to be imminent. A reduction or increase in myocardial conduction velocity without a change in propagation direction will apparently not be detected.

In the specific environment of the present invention where it is necessary to accurately and reproductively measure very small time intervals, prior art sense amplifiers are not optimal. The presentation of the atrial or ventricular depolarization wave front across the two spaced electrodes varies from patient to patient and, from time to time, in the same patient. This presentation may affect the rise time amplitude and polarity of the electrical depolarization wave front signal and affect the trigger point of the sense amplifier, leading to inaccurate interval data.

SUMMARY OF THE INVENTION

It is the object of the present invention to provide a system for measuring myocardial conduction velocity and deriving control signals therefrom for controlling the delivery of electrical or other therapy to the heart or for monitoring or diagnostic purposes.

In one embodiment of the invention this system is used to provide a method and apparatus for automatically adjusting the pacing rate of a pacemaker as a function of physiologic need as evidenced by the myocardial conduction velocity of depolarization wave fronts. This embodiment of the invention comprises means for applying electrical stimulating pulses to the heart through at least one electrode in contact with heart tissue and another electrode; means for detecting a cardiac event potential at a first sensing electrode spaced from said first electrode by a predetermined distance; field density clamp sensing means for detecting said cardiac event potential at a second sensing electrode spaced a second predetermined distances from said first sensing electrode; means for deriving a time difference signal my measuring the time difference between the detection of said cardiac event potentials at said second sensing electrode with respect to said first sensing electrode; means for comparing said time difference signal with a table of values representing an appropriate heart rate for maintaining the detected velocity of wave front propagation manifested by the time difference signal and providing a pacing rate control signal in response thereto; and means for controlling the rate of said electrical stimulating pulses applied to the heart in response to said rate control signal.

This embodiment of the present invention is thus directed to an improved pacemaker pulse generator and lead system which relies upon the myocardial conduction velocity of natural or evoked depolarization wave fronts within the syncytium of the heart which advantageously avoids the necessity for a special sensor. However, the disclosed system for sensing changes in conduction velocity may also be used for other purposes, such as for detecting the presence of pathologic conditions such as gross myocardial hypoxia or ischemia or monitoring the delivery of cardiac drugs, any of which may alter the conduction velocity of the heart. In such embodiments of the invention, the system may also be used for controlling delivery of other pacing or electrical therapies, cardioversion or defibrillation or to control systemic or local delivery of cardiac drugs.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

In the following description, reference is made to an illustrative embodiment for carrying out the invention. It is understood that other embodiments may be utilized without departing from the scope of the invention.

Figure 1:
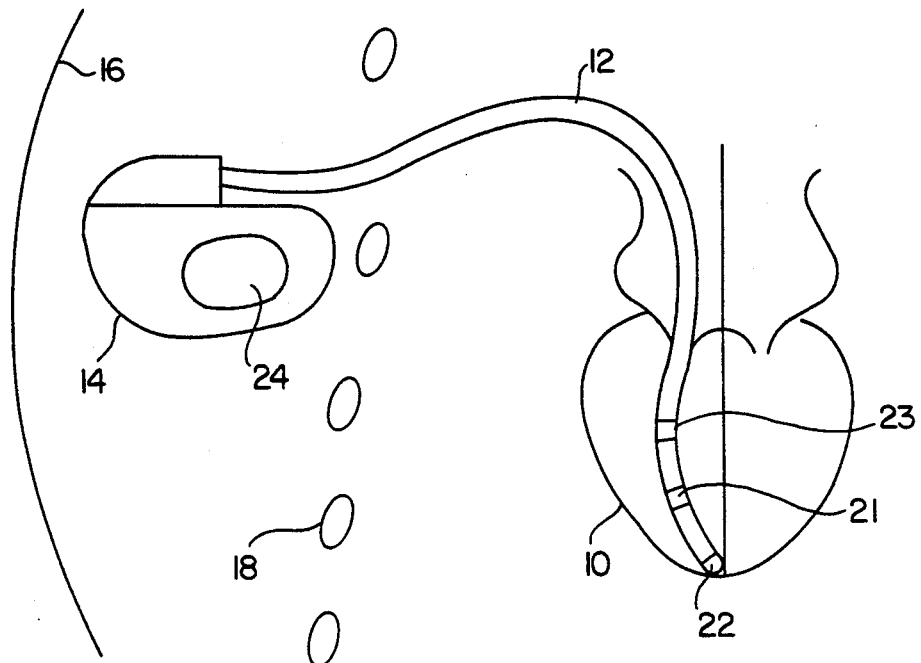
FIG. 1 is a schematic diagram depicting the interconnection between the pacer and the heart.

FIG. 1 is a schematic diagram depicting the interconnection between the pacer and the heart. A ventricular inhibited pacer is shown with a lead bearing three electrodes situated in the ventricle.

The pacemaker 14 is implanted beneath the skin 16, outside the rib-cage 18. A pacing lead 12 is passed pervenously into the right ventricle of the heart 10. The pacing lead 12 is used for supplying pacing pulses to the heart and for conducting electrical signals resulting from the depolarization of the heart to the pacemaker 14. Lead 12 carries a tip electrode 22, and ring electrodes 21 and 23. The pacemaker housing includes an uninsulated area 24 which may also function as an electrode. As illustrated, the tip and ring electrodes 22 and 21 are spaced apart between 0.5 and 3.0 cm, as are ring electrodes 21 and 23. In dual chamber pacemakers, an additional lead carrying one or more electrodes would be situated in or on the atrium or coronary sinus. Ring electrodes 21 and 23 may be conventional ring electrodes as are widely used on pacing leads as indifferent electrodes, and may have surface areas of about 35 square millimeters or less.

Figure 2:
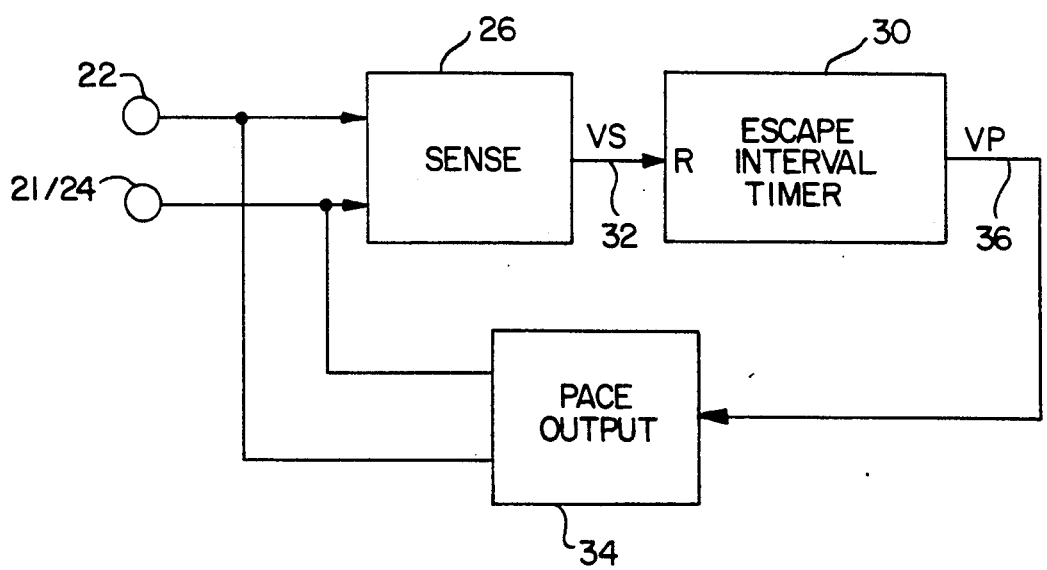
FIG. 2 is a block diagram depicting the relationship between the sense amplifier and the other circuitry of a simplified single chamber pacemaker pulse generator.

FIG. 2 depicts the major circuit elements contained within a typical, prior art ventricular demand pacer. The tip electrode and the ring electrode 21 or the case electrode and 24 are electrically coupled to the sense amplifier 26. In operation, the sense amplifier 26 detects the occurrence of the cardiac depolarization and generates a ventricular sense signal (VS) which is coupled to the escape interval timer 30 through an electrical connection 32. Typically, the escape interval timer is remotely programmed to a ventricular escape interval which corresponds to the desired minimum time interval between heartbeats. The occurrence of a ventricular sense event (VS) resets the escape interval timer and thus resynchronizes the pacer to the underlying rhythm of the patient's heart. If no ventricular sense event occurs within the escape interval the escape interval timer times out and generates a ventricular pace signal (VP) which is provided to the pulse generator circuit 34 through a suitable electrical connection 36. The output of the simulation pulse generator is electrically coupled to the tip electrode and delivers a suitable stimulation pulse between the tip electrode 22 and the ring electrode 21 or the case electrodes 24. The amplitude of the stimulation pulse is chosen to trigger electrical depolarization of the heart tissue and mechanical contraction of the heart muscle, as is conventional in cardiac pacers.

Returning to FIG. 1, in accordance with the present invention a second ring electrode 23 is shown spaced more proximately from tip electrode 22 than ring electrode 21. The present invention involves the measurement of the time that elapses from the detection of a depolarization wave front at one of the ring electrodes, until detection at the other ring electrode. The ring electrodes may be referenced to either the tip electrode 22 or the case electrode 24. While it is possible to employ conventional bipolar pacing leads to measure the wave front, it is preferable to employ two or more spaced ring electrodes 21, 23, and to provide the pulse generator with a programmable switching network so that the optimal electrode spacing for greatest specificity of response may be selected by the physician for the individual patient.

In experiments conducted with the sense amplifiers described in reference to FIG. 3 below, two ring electrodes 21 and 23, spaced 1.5 cm and 2.8 cm from the tip electrode 22 in a single lead 12 were implanted in canines and tests were conducted verifying the concept of the present invention. In these tests, a stimulating pulse was delivered between the tip electrode 22 and the case electrode 24. The evoked response signal, which is a projection of the disturbance associated with the passage of the myocardial depolarization wave front, is presented first to the most distal ring electrode 21, and then to the more proximal electrode 22. The elapsed time between the detected peaks of the evoked response signal varies as a function of the myocardial contractility which itself varies as a function of physiological demand on the cardiovascular system.

In order to provide reproducible results, it is necessary that the sense amplifiers coupled to ring electrodes 21 and 23 (and, in each case to either tip electrode 22 or case electrode 24) respond to the highest frequency components of the wave front and disregard the lower frequency components. The sense amplifier illustrated in FIG. 3 accomplishes this desired result.

Figure 3:
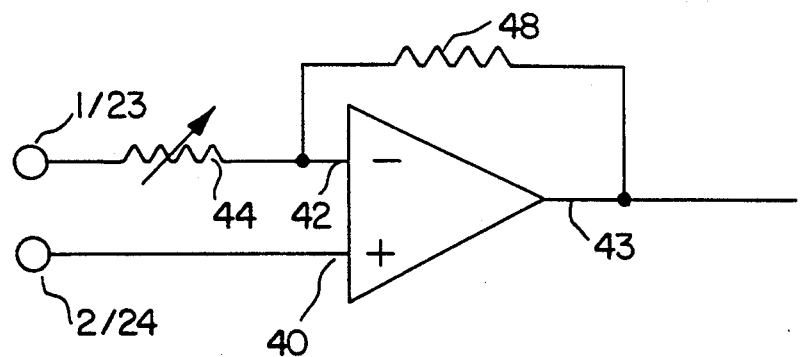
FIG. 3 is a schematic diagram of an illustrative field density clamp sense amplifier circuit for carrying out the invention.

FIG. 3 is a schematic diagram of an illustrative circuit for carrying out the detection of the change in conduction velocity of the invention. An operational amplifier (op amp) 38 has its noninverting input 40 connected to the tip or case electrode 22 or 24. The inverting input 42 is connected to either ring electrode 21 or 23. The ring electrode is coupled to terminal 42 through a variable resistor 44 which is used to set a virtual load resistance for the system. In operation, the amplifier 38 maintains its inputs at equal electrical potentials. Maintaining the inputs at equal potentials requires delivery of electrical current through feedback resistor 48 and virtual load resistor 44 to the ring electrode such that the voltage drop across the virtual load resistor corresponds to the potential difference between the electrodes resulting from the depolarization induced disturbance of the previous equilibrium condition. Control of the current through the virtual load resistor is accomplished by varying the voltage at the output 43 to produce the required voltage drop across virtual load resistor 44. The op amp 38 thus provides a signal at output 43 which reflects the amount of current delivered through the virtual load 44 in response to the passage of the depolarization wavefront. This amplifier circuit is discussed in more detail in the above cited applications by Hudrlik.

Because the virtual load resistor is low valued, (e.g. 1000 ohms or less) the current flow through the virtual load quickly counteracts the depolarization induced charge imbalance in the vicinity of the ring electrode. The amplifier 26 thus works to maintain the charge equilibrium condition preceding the depolarization, even as the depolarization occurs, and quickly restores the equilibrium condition following passage of the depolarization wavefront.

Ordinary bioengineering amplifier design practices dictate that an amplifier's input impedance must be at least an order or magnitude higher than the source impedance. See for example, "Bioelectric Amplifier", in *Introduction to Biomedical Equipment Technology* by Carr and Brown, John Wiley & Sons, 1981, pages 41-44 at 42. In accordance with the present invention, however, the input impedance of operation amplifier 38 may be varied by adjustment of resistor 44 to be equal to or substantially less than the source impedance which, in the case of heart tissue, typically is in the range of 500-1000 ohms. The detuning of the sense amplifier results in sharply enhanced peaks in the signal at point 43 as the operational amplifier works to maintain the charge equilibrium condition at the electrodes.

Figure 4:
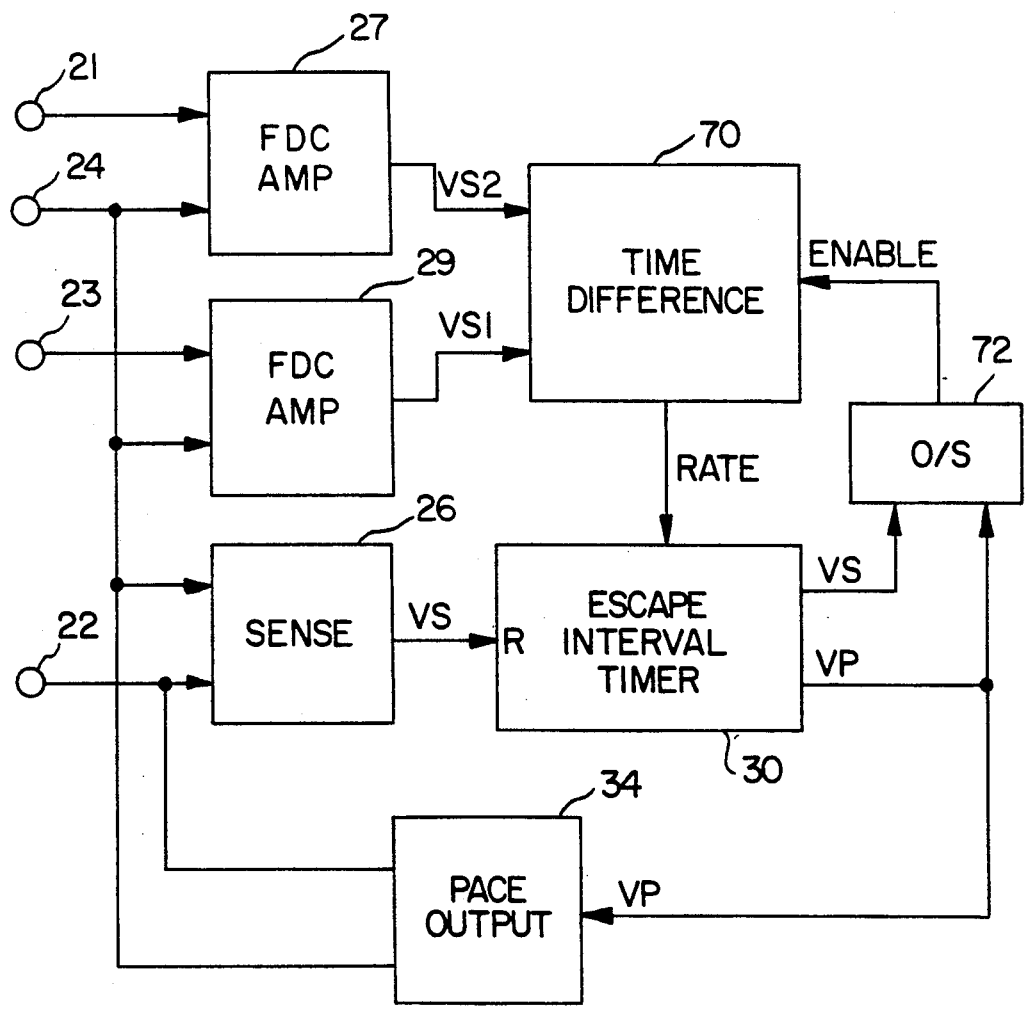
FIG. 4 is a block diagram depicting how the sense amplifier circuits of FIG. 3 may be introduced into the block diagram of FIG. 2 to effect a rate responsive pacing mode of operation.

FIG. 4 illustrates the connection of the field density clamp sense amplifiers 27 and 29 to a variable rate, single chamber pacemaker in accordance with the invention. The field density clamp sense amplifiers 27 and 29 are coupled to ring electrodes 21 and 23, respectively and to case electrode 24. The output signals VS1 and VS2 (which correspond to signal VS in FIG. 3) are applied to a time difference circuit 70, which when enabled by one shot 72, provides a rate control signal to the rate input of the escape interval timer 30. The time difference circuit 70 is enable by one shot 72 or the one shot time period (10-100 milliseconds) each time that the one shot is triggered by the delivery of a pace trigger signal by the escape interval timer circuit. The time difference measurement circuit may correspond to that disclosed in U.S. Pat. No. 4,750,494 issued to King on Jun. 14, 1988, incorporated herein by reference in its entirety. In the King patent, differences in relative arrival time of depolarization wavefronts at multiple electrode sets are used to measure changes in depolarization wavefront propagation direction, rather than changes in conduction velocity, as part of a system for detecting impending fibrillation.

The time difference circuit 70 is normally disabled during the delivery of a pace stimulus and for a short time period up to 10 milliseconds thereafter to allow the fast recharge circuits of the pacing pulse generator to dissipate polarization potentials on electrodes 22 and 24. In addition, the time difference circuit 70 is disabled after the 100 millisecond window in order to avoid developing a rate control signal due to spontaneous ectopic ventricular depolarizations that may occur after the refractory periods. In addition, the one shot 72 may be enabled by a separate timer within the escape interval timer block 70 at a preset percentage (such as 75%) of the last most recent escape interval to insure that the one shot time window overlaps the delivery of a pacing stimuli or the heart's spontaneous depolarization.

In the case of a spontaneous depolarization, the time difference may, however, vary from that associated with a paced beat, depending on the orientation of the ring electrodes to the direction of propagation of the natural depolarization wave front as per the above-cited King patent. In such case, it may be necessary to provide a separate weighting factor to the elapsed time signal developed by the time difference circuit 70. The separate weighing factor may be applied depending on whether or not a paced trigger signal precedes the calculated time difference signal.

The invention as illustrated in FIG. 4 may be implemented employing a multiprogrammable, multimode, processor based interval measurement and analysis system of the type described in the aforementioned King patent, and the time difference and the one shot window intervals may be effected by the processor under software algorithm control. Preferably, in addition, the pulse generator 34 would include fast recharge circuitry, as mentioned above, known in the art for rapidly discharging repolarization potentials on electrodes 22 and 24 within 10 milliseconds after delivery of a pacing impulse typically of 0.5 milliseconds duration. Alternatively, as disclosed in the above-cited Hudrlik Application Ser. No. 07/730,160, and FDC amplifier may be employed as a stimulation pulse generator, also providing rapid recovery of the electrodes following delivery of a pacing pulse.

The rate control signal developed by the time difference circuit will provide desired pacing rates as a function of the measured conduction velocity and rate of change of conduction velocity, in a fashion generally corresponding to the rate control systems for controlling temperature sensing pacemakers, as disclosed in the above cited U.S. Pat. No. 4,543,954, issued to Cook et al. and incorporated herein by reference in its entirety. The heat developed by muscle tissue during exercise raises the temperature of the blood leaving it. This blood returns directly to the right heart before passing through heat dissipating tissue. The blood returning to the right heart therefore contains information about the work output of the body muscle mass.

Right ventricular blood is a combination of blood from the upper body via the superior vena cava and from the lower body via the inferior vena cava. The blood from these two areas of the body is mixed in the right atrium and again in the right ventricle where the electrodes 22, 21 and 23 reside. The right ventricular blood temperature is the average temperature returning from all of the body including the blood drained from the heart and so reflects the average work output of the body. It has been observed experimentally that the conduction velocity of the myocardial depolarization wave front rises and falls with right ventricular blood temperature. Generally, as the blood temperature rises with exercise, the speed of propagation of the depolarization wave front likewise increases. Conversely, as blood temperature falls, as exercise level decreases, so does the speed of propagation of the depolarization wave front. Thus, the measured conduction velocity may be substituted for the measured temperature, and used to control pacing rate.

While the detection of blood temperature requires a temperature sensor, advantageously, the present invention requires only sensing electrodes for detecting the passage of the depolarization wave front across the spaced electrodes and providing sharply defined and specific time intervals representative of the slight increases and decreases in the velocity of wave front as influenced by blood temperature changes in response to exercise. Thus the present invention may advantageously be implemented with conventional pacing technology normally drawing very little current from the power source and requiring no more than the single additional electrode and conductor in the lead system employed with the pulse generator.

In the teachings of the present invention, it may be contemplated that the rate may be adjusted between a programmable lower rate limit and a programmable upper rate limit by a linear or other increasing progression in pacing rate relative to change in the velocity of the depolarization wave front as measured by the time difference circuit 70. In accordance with the teachings of the prior art, the slope of the progression between the lower rate limit and the upper rate limit may be programmed by the physician to provide the optimum pacing rate response to the individual patient's actual rate of change of depolarization wave front velocity with exercise during patient workup.

The function relating the measured conduction velocity to a desired pacing rate may be embodied in a look-up table within the memory of the pacemaker. Alternatively, the pacemaker may include arithmetic logic and calculate the pacing rate based on the measured conduction velocity. Both of these general approaches to regulating rate as a function of sensor output are well known to the art and have been described in numerous prior U.S. Patents including 5,063,927 issued to Webb et al., 5,092,388 issued to Silula et al., 4,856,522 issued to Hanson and 4,708,143 issued to Schroeppel, all of which are incorporated herein by reference in their entireties.

While the disclosed embodiment of the invention employs the myocardial conduction velocity measurement to control pacing rate, the measurement of conduction velocity may also be employed solely for diagnostic purposes or to control delivery of therapies other than bradycardia pacing. For example, as discussed above, changes in conduction velocity may also be related to myocardial ischemia. In the context of an implantable pacemaker/cardioverter/defibrillator, a measured change of conduction velocity in conjunction with a heart rate indicative of tachycardia may be used to select an antitachycardia therapy. Changes in myocardial conduction velocity are also related to changes in sympathetic tone of the heart muscle, and thus may also be useful in this context to predict the onset of fibrillation, to assist a pacemaker/cardioverter/defibrillator in providing therapy directed to the avoidance or termination of the fibrillation. As discussed above, changes in conduction velocity may also occur in conjunction with use of certain cardiac drugs. In the context of an implantable drug dispenser, feedback control of the delivery of such drugs may be accomplished by means of measured conduction velocity. Therefore, the disclosed embodiment of the present invention should be considered exemplary, rather than limiting with regard to the claims which follow.

What is claimed is:

1. A cardiac pacemaker, comprising:
    means for applying cardiac pacing pulses to the heart for triggering depolarizations and corresponding mechanical contractions of said heart;
    first and second spaced electrodes adapted for location on or in the same chamber of said heart;
    means coupled to said first and second electrodes for detecting the times at which a depolarization wavefront sequentially passes said first and second electrodes and for measuring the time interval therebetween; and
    means for controlling the rate of said cardiac pacing pulses applied to said heart to vary as a function of said measured time interval.

2. The cardiac pacemaker of claim 1 further comprising a third electrode, wherein said detecting means comprises amplifier means which in turn comprises a virtual load impedance coupled to at least one of said first and second electrodes and an active circuit means for delivering electrical current to said at least one of said first and second electrodes through said virtual load to counteract depolarization induced disturbances in the charge equilibrium condition between said at least one of said first and second electrodes and said third electrode, and wherein said detecting further comprises means responsive to the delivery of electrical current through said virtual load impedance for detecting the passage of a depolarization wavefront past said at least one of said first and second electrodes.

3. The cardiac pacemaker of claim 2 wherein said detecting means comprises two of said amplifier means each coupled to one of said first and second electrodes.

4. The cardiac pacemaker of claim 3 wherein said amplifier means each comprise an operational amplifier having positive and negative inputs and an output, a feedback impedance coupled between said negative input and said output, a virtual load impedance coupled between one of said first and second electrodes and said negative input, said positive input coupled to said third electrode means.

5. The cardiac pacemaker of claim 1 wherein said first and second electrodes are spaced apart a distance in the range of 0.5–3.0 cm.

6. An implantable therapeutic device, comprising:
means for applying a therapy to the body of a patient;
first and second electrodes, spaced from one another and adapted for location on or in the same chamber of the heart of said patient;
a third electrode;
means coupled to said first and second electrodes for detecting the times at which a depolarization wavefront sequentially passes said first and second electrodes and for measuring the time interval therebetween;
wherein said detecting means comprises amplifier means which in turn comprises a virtual load impedance coupled to at least one of said first and second electrodes and an active circuit means for delivering electrical current to said at least one of said first and second electrodes through said virtual load to counteract depolarization induced disturbances in the charge equilibrium condition between said at least one of said first and second electrodes and said third electrode, and wherein said detecting further comprises means responsive to the delivery of electrical current through said virtual load impedance for detecting the passage of a depolarization wavefront past said at least one of said first and second electrodes; and
means for controlling the application of said therapy to the body of said patient as a function of said measured time interval.

7. A device according to claim 6 wherein said detecting means comprises a said amplifier means coupled to each of said first and second electrodes.

8. A device according to claim 7 wherein said amplifier means each comprise an operational amplifier having positive and negative inputs and an output, a feedback impedance coupled between said negative input and said output, a virtual load impedance coupled between one of said first and second electrodes and said negative input, said positive input coupled to said third electrode means and said output of said operational amplifier coupled to said responsive means.

9. A device according to claim 6 wherein said first and second electrodes are spaced apart a distance in the range of 0.5–3.0 cm.

10. A device according to claim 6 wherein said means for applying said therapy comprises means for applying cardiac pacing pulses to the heart for triggering depolarizations and mechanical contractions of said heart and wherein said controlling means comprises means for controlling the rate of said cardiac pacing pulses applied to said heart as a function of said measured time interval.

11. An implantable device, comprising:
first and second electrodes, spaced from one another and adapted for location on or in the same chamber of the heart of a patient;
a third electrode; and
means coupled to said first and second electrodes for detecting the times at which a depolarization wavefront sequentially passes said first and second electrodes and for measuring the time interval therebetween, said detecting means comprising amplifier means which in turn comprises a virtual load impedance coupled to at least one of said first and second electrodes and an active circuit means for delivering electrical current to said at least one of said first and second electrodes through said virtual load to counteract depolarization induced disturbances in the charge equilibrium condition between said at least one of said first and second electrodes and said third electrode, and wherein said detecting further comprises means responsive to the delivery of electrical current through said virtual load impedance for detecting the passage of a depolarization wavefront past said at least one of said first and second electrodes.

12. A device according to claim 11 wherein said detecting means comprises a said amplifier means coupled to each of said first and second electrodes.

13. A device according to claim 12 wherein said amplifier means each comprise an operational amplifier having positive and negative inputs and an output, a feedback impedance coupled between said negative input and said output, a virtual load impedance coupled between one of said first and second electrodes and said negative input, said positive input coupled to said third electrode means and said output of said operational amplifier coupled to said responsive means.

14. A device according to claim 11 wherein said first and second electrodes are spaced apart a distance in the range of 0.5–3.0 cm.

15. A cardiac pacemaker, comprising:
means for applying cardiac pacing pulses to the heart for triggering depolarizations and mechanical contractions of said heart;
means for measuring the conduction velocity of a myocardial depolarization wavefront within a single chamber of said heart; and
means for controlling the rate of said cardiac pacing pulses applied to said heart to vary as a function of said measured conduction velocity.

16. The cardiac pacemaker of claim 15 further comprising first and second electrodes, wherein said measuring means comprises amplifier means which in turn comprises a virtual load impedance coupled to said first electrode and an active circuit means for delivering electrical current to said first electrode through said virtual load to counteract depolarization induced disturbances in the charge equilibrium condition between said at least one of said first and second electrodes and said third electrode, and wherein said measuring means further comprises means responsive to the delivery of electrical current through said virtual load impedance for determining the conduction velocity of a depolarization wavefront past said first electrode.

17. The cardiac pacemaker of claim 16 wherein said amplifier means comprises an operational amplifier having positive and negative inputs and an output, a feedback impedance coupled between said negative input and said output, a virtual load impedance coupled between said first electrode and said negative input, said positive input coupled to said second electrode and said output of said operational amplifier coupled to said determining means.

18. An apparatus for measuring conduction velocity of a depolarization wavefront in a single chamber in a heart, comprising:
first and second electrodes;

amplifier means which in turn comprises a virtual load impedance coupled to said first electrode and an active circuit means for delivering electrical current to said first electrode through said virtual load to counteract depolarization induced disturbances in the charge equilibrium condition between said first and second electrodes; and means responsive to the delivery of electrical current through said virtual load impedance for determining the conduction velocity of a depolarization wavefront past said first electrode.

19. The cardiac pacemaker of claim 18 wherein said amplifier means comprises an operational amplifier having positive and negative inputs and an output, a feedback impedance coupled between said negative input and said output, a virtual load impedance coupled between said first electrode and said negative input, said positive input coupled to said second electrode and said output of said operational amplifier coupled to said determining means.

* * * * *